(12) United States Patent
Chawla

(10) Patent No.: US 8,936,565 B2
(45) Date of Patent: *Jan. 20, 2015

(54) SELECTIVE ALARMS FOR AN INFUSION DEVICE

(71) Applicant: Medtronic MiniMed, Inc., Northridge, CA (US)

(72) Inventor: Hiten Chawla, Santa Monica, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 218 days.

This patent is subject to a terminal disclaimer.

(21) Appl. No.: 13/650,006

(22) Filed: Oct. 11, 2012

(65) Prior Publication Data

US 2013/0035633 A1 Feb. 7, 2013

Related U.S. Application Data

(63) Continuation of application No. 13/094,469, filed on Apr. 26, 2011, now Pat. No. 8,308,680.

(51) Int. Cl.
*A61M 5/168* (2006.01)
*G08B 1/08* (2006.01)
*A61M 5/00* (2006.01)
*A61M 5/142* (2006.01)

(52) U.S. Cl.
CPC .............. *A61M 5/00* (2013.01); *A61M 2205/18* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/505* (2013.01); *A61M 2205/52* (2013.01); *A61M 2205/581* (2013.01); *A61M 2205/582* (2013.01); *A61M 2209/01* (2013.01); *A61M 2230/201* (2013.01); *A61M 5/14248* (2013.01)
USPC .............................. 604/67; 607/60; 340/539.1

(58) Field of Classification Search
USPC .................... 604/67; 702/97, 158, FOR. 145, 702/FOR. 146, FOR. 147; 607/2, 60; 304/539.1
See application file for complete search history.

(56) References Cited

U.S. PATENT DOCUMENTS

| | | | | | |
|---|---|---|---|---|---|
| 5,027,314 | A | * | 6/1991 | Linwood et al. | 701/300 |
| 5,357,254 | A | * | 10/1994 | Kah, Jr. | 342/42 |
| 5,461,390 | A | * | 10/1995 | Hoshen | 342/419 |
| 5,558,640 | A | * | 9/1996 | Pfeiler et al. | 604/67 |
| 5,650,770 | A | * | 7/1997 | Schlager et al. | 340/573.1 |
| 5,652,570 | A | * | 7/1997 | Lepkofker | 340/573.4 |
| 6,641,533 | B2 | * | 11/2003 | Causey et al. | 600/300 |
| 7,931,613 | B2 | * | 4/2011 | Haueter et al. | 604/66 |

(Continued)

*Primary Examiner* — Quynh-Nhu H Vu
(74) *Attorney, Agent, or Firm* — Medtronic Minimed, Inc.

(57) ABSTRACT

An infusion system to administer a fluid includes an infusion pump with a pump processor, a pump memory to store a plurality of configurable alarms and a pump radio to enable bi-directional communication. The infusion system further includes a controller that has a controller processor, a controller memory, a controller radio to transmit and receive communication from the pump radio. The controller further has a graphical user interface shown on a display along with controls to manipulate the graphical user interface. Furthermore, the bi-directional communication between the infusion pump and the controller establish an infusion pump relative proximity between the infusion pump and the controller such that when the infusion pump relative proximity exceeds a pump threshold distance at least one of the plurality of configurable alarm conditions of the infusion pump is modified.

16 Claims, 4 Drawing Sheets

(56) References Cited

U.S. PATENT DOCUMENTS

| | | | |
|---|---|---|---|
| 8,308,680 B1 * | 11/2012 | Chawla | 604/67 |
| 2007/0124002 A1 * | 5/2007 | Estes et al. | 700/20 |
| 2007/0243855 A1 * | 10/2007 | Hoffman et al. | 455/404.2 |
| 2008/0132844 A1 * | 6/2008 | Peterson et al. | 604/151 |
| 2009/0005729 A1 * | 1/2009 | Hendrixson et al. | 604/67 |

* cited by examiner

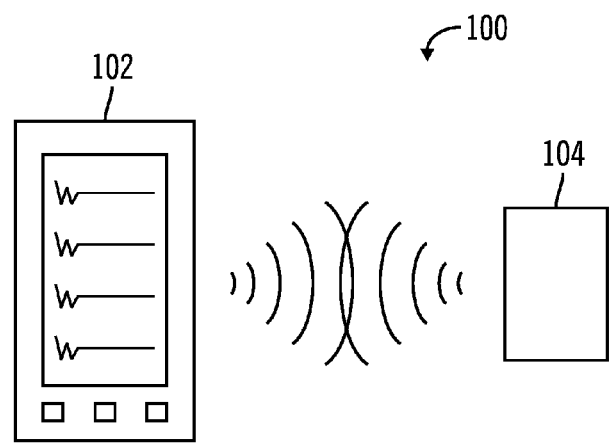
FIG. 1
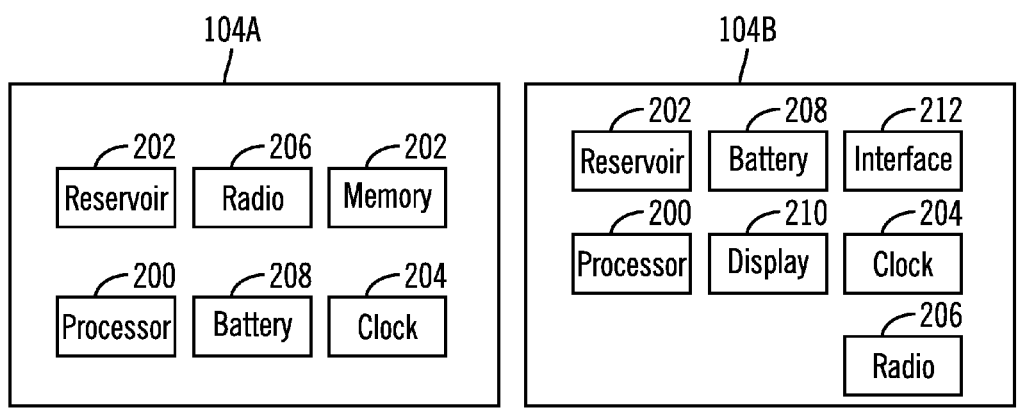
FIG. 2A
FIG. 2B

SELECTIVE ALARMS FOR AN INFUSION DEVICE

FIELD OF THE INVENTION

This invention relates to monitor systems and, in particular embodiments, to devices and methods for monitoring of a sensor to determine a characteristic of a body.

BACKGROUND OF THE INVENTION

Over the years, bodily characteristics have been determined by obtaining a sample of bodily fluid. For example, diabetics often test for blood glucose levels. Traditional blood glucose determinations have utilized a painful finger prick using a lancet to withdraw a small blood sample. This results in discomfort from the lancet as it contacts nerves in the subcutaneous tissue. The pain of lancing and the cumulative discomfort from multiple needle pricks is a strong reason why patients fail to comply with a medical testing regimen used to determine a change in characteristic over a period of time. Although non-invasive systems have been proposed, or are in development, none to date have been commercialized that are effective and provide accurate results. In addition, all of these systems are designed to provide data at discrete points and do not provide continuous data to show the variations in the characteristic between testing times.

A variety of implantable electrochemical sensors have been developed for detecting and/or quantifying specific agents or compositions in a patient's blood. For instance, glucose sensors have been developed for use in obtaining an indication of blood glucose levels in a diabetic patient. Such readings are useful in monitoring and/or adjusting a treatment regimen which typically includes the regular administration of insulin to the patient. Thus, blood glucose readings improve medical therapies with semi-automated medication infusion pumps of the external type, as generally described in U.S. Pat. Nos. 4,562,751; 4,678,408; and 4,685,903; or automated implantable medication infusion pumps, as generally described in U.S. Pat. No. 4,573,994, which are herein incorporated by reference. Typical thin film sensors are described in commonly assigned U.S. Pat. Nos. 5,390,671; 5,391,250; 5,482,473; and 5,586,553 which are incorporated by reference herein, also see U.S. Pat. No. 5,299,571. However, the monitors for these continuous sensors provide alarms, updates, trend information and require sophisticated hardware to allow the user to program the monitor, calibrate the sensor, enter data and view data in the monitor and to provide real-time feedback to the user. This sophisticated hardware makes it most practical for users that require continuous monitoring with feedback to maintain tight control over their conditions. In addition, these systems require the user to be trained in their use, even if to be worn for short periods of time to collect medical data which will be analyzed later by a doctor.

The medication infusion pumps often have multiple alarms that can remind users of specific events or times. These alarms may be delivered to the user in any different combinations or even singly with tactile vibrations, different audible tones, or visually with various flashing or blinking lights. However there may be certain situations where an individual would rather not have extraneous vibrations, tones or lights flashing.

SUMMARY OF THE DISCLOSURE

In one embodiment an infusion system to administer a fluid is disclosed. The infusion system includes an infusion pump having a pump processor, a pump memory and a pump radio to enable bi-directional communication. The pump memory stores a plurality of configurable alarm conditions. The infusion system further includes a controller that has a controller processor, a controller memory, a controller radio to transmit and receive communication from the pump radio. The controller further has a graphical user interface shown on a display. Also included with the controller are controls to manipulate the graphical user interface. Furthermore, the bi-directional communication between the infusion pump and the controller establish an infusion pump relative proximity between the infusion pump and the controller such that when the infusion pump relative proximity exceeds a pump threshold distance at least one of the plurality of configurable alarm conditions of the infusion pump is modified.

In another embodiment, an infusion system to administer a fluid is disclosed. The infusion system includes an infusion pump that has a pump processor, a pump memory and a pump radio to enable bi-directional communication. The pump memory used to store a plurality of configurable alarm conditions. The infusion system further includes a sensor assembly having a sensor to be placed within an analyte. The sensor assembly further has a sensor radio to enable bi-directional communication with the controller and provide continuous monitoring of the analyte. The infusion system also includes a controller that has a controller processor, a controller memory, a controller radio to transmit and receive communication from the pump radio. Additionally, the controller further has a graphical user interface shown on a display. The controller for the infusion system also includes controls to manipulate the graphical user interface. The bi-directional communication between the infusion pump and the controller establish an infusion pump relative proximity between the infusion pump and the controller such that when the infusion pump relative proximity exceeds a pump threshold distance a prompt is delivered to request user confirmation to modify at least one of the plurality of configurable alarm conditions of the infusion pump.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 1 is an exemplary illustration of components of an infusion system, in accordance with embodiments of the present invention.

FIGS. 2A and 2B are exemplary block diagrams illustrating select components of two types of infusion pumps, in accordance with embodiments of the present invention.

DETAILED DESCRIPTION

Figure 3A:
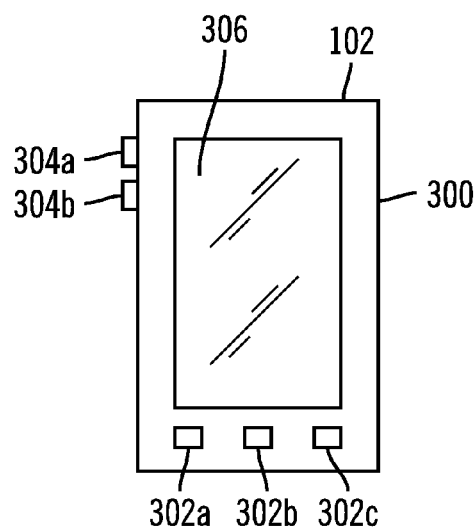
FIG. 3A is an exemplary depiction of controller, in accordance with an embodiment of the present invention.

As shown in the drawings for purposes of illustration, the invention is embodied in an infusion system. The infusion system may include an infusion pump, a controller and a sensor assembly. The controller can be used to receive and transmit data from the infusion pump and the sensor. Wireless data transmission can also be used to determine a relative distance separating the controller and the infusion pump. Sensor data can be recorded and stored in a memory associated with the controller. In embodiments of the present invention, the analyte sensor set and monitor system are for determining glucose levels in the blood and/or bodily fluids of the user without the use of, or necessity of, complicated monitoring systems that require user training and interaction. However, it will be recognized that further embodiments of the invention may be used to determine the levels of other analytes or agents, characteristics or compositions, such as hormones, cholesterol, medications concentrations, viral loads (e.g., HIV), or the like. In other embodiments, the monitor system may also include the capability to be programmed to record data at specified time intervals. The monitor system and analyte sensor are primarily adapted for use in subcutaneous human tissue. However, still further embodiments may be placed in other types of tissue, such as muscle, lymph, organ tissue, veins, arteries or the like, and used in animal tissue. The analyte sensors may be subcutaneous sensors, transcutaneous sensors, percutaneous sensors, sub-dermal sensors, skin surface sensors, or the like. Embodiments may record sensor readings on an intermittent or continuous basis.

FIG. 1 is an exemplary illustration of components of an infusion system 100 that includes a controller 102 and an infusion pump 104, in accordance with embodiments of the present invention. In one embodiment the infusion pump 104 has minimal controls and the controller 102 is the primary interface device to program and verify setting of the infusion pump 104. In one embodiment the controller 104 exchanges data with the infusion pump 104 via bi-directional wireless communications facilitated by radios, optical interconnections such as infra-red or the like. In other embodiments, data transmission between the infusion pump 104 and the controller 102 can be performed via a wired connection.

In embodiments where the infusion pump 104 and the controller 102 communicate wirelessly, the controller 102 can be used to configure or program an associated infusion pump 104 to deliver a basal rate. Additionally, in some other embodiments the controller 102 can be used to program the infusion pump 104 to periodically remind a user via an alarm to deliver a bolus. Once the infusion pump 104 is programmed using the controller 102, the infusion pump 104 can execute the program without further interaction from the controller 102.

For example, using the controller 102 an infusion pump 104 is programmed to deliver a basal rate. Once programmed, the infusion pump 104 will deliver the basal rate without further input from the controller 102 until either a fluid reservoir within the infusion pump is exhausted via the basal rate, the power supply to the infusion pump is exhausted, or another type of delivery failure. Thus, after the infusion pump 104 is programmed, the infusion pump 104 will execute the program independent of the controller 102. The controller 102 can be used to modify or augment the program of an infusion pump 104, however, the infusion pump 104 does not require continual or periodic updates from the controller 102 to execute a stored program.

FIGS. 2A and 2B are exemplary block diagrams illustrating select components of two types of infusion pumps 104A and 104B, in accordance with embodiments of the present invention. In one embodiment the infusion pump 104A illustrated in FIG. 2A is a patch pump that is designed to be affixed directly to a user's skin while infusion pump 104B is an external infusion pump such as the Medtronic Minimed Paradigm Revel. As illustrated, the infusion pump 104B includes both a display 210 and an interface 212 that are not found on the infusion pump 104A. In some embodiments the display 210 and the interface 212 found on infusion pump 104B may duplicate some of the control functionality provided by the controller 102 (FIG. 1). While infusion pump 104A does not explicitly have an interface 212, the embodiment illustrated should not be construed to preclude an interface. Infusion pump 104A and similar patch pumps may include interface features such as, but not limited to, buttons, lights, and the like. Both infusion pumps 104A and 104B include a reservoir 202 that contains a fluid that is infused into a user. Additionally, the infusion pumps 104A and 104B also have a processor 200, a memory 202, a clock 204, a radio 206, and a battery 208.

In one embodiment the memory 202 is used to store program instructions that are executed by the processor 200. The memory 202 may also used to store settings for the infusion pump 104 such as, but not limited to, basal rates and bolus values for various times of day. In embodiments where the infusion pump 104 is used to deliver insulin, the memory 202 can be used to store information specific to a user such as, but not limited to a carbohydrate-to-insulin ratio (CM) and an insulin sensitivity factor (ISF) of a user. In all embodiments, the memory 202 may be used in conjunction with the clock 204 to store various alarms. Some of the various alarms that are associated with the clock 204 are periodic notifications of an infusion or periodic notifications that the user should perform a check of their blood glucose value. Furthermore, the memory 202 can be used to store threshold values to trigger various alarms to notify a user of issues discovered during a diagnostic test of the infusion pump. For example, the memory 202 can include threshold values to determine if there is occlusion of the infusion site, an infusion line, or if a battery needs to be replaced. The types of threshold alarms discussed above are merely exemplary and should not be construed as limiting.

The alarms are conveyed to a user either audibly or tactilely. Audible alarms can include, but are not limited to audible beeps, chirps, and polyphonic ringtones. Furthermore, a user can adjust the volume of the audible alarms using a simple rocker switch associated with either the controller 102, the infusion pump 104 or in some embodiments, both the controller 102 and the infusion pump 104. In other embodiments another type of user interface, such as a slider displayed via a graphic user interface, a click-wheel type device, or a knob, on the controller 102, the infusion pump 104 or both, can be used to adjust the volume of the alarms. Tactile alarms can be conveyed to the user via vibration from the controller 102, the infusion pump 14 or both. In some embodiments the intensity of the tactile alarms can be adjusted so the tactile alarms are relatively discrete.

The audible alarms and tactile alarms can use different sequences of tones or vibrations to indicate various alarm states. Additionally, the various alarms of the infusion pump can be categorized as a delivery alarm or a non-delivery alarm. Events that trigger a delivery alarm are directly associated with delivery of fluid from the infusion pump. Some examples if alarms that could be categorized as delivery alarms are low battery warnings, a low fluid in the reservoir warning, failure to deliver fluid, or another type of system error that would directly affect fluid delivery. Some examples of alarms that could be categorized as non-delivery alarms are predetermined times for blood glucose checks, predetermined alarms that remind a patient it may be time for a bolus, and alarms to remind a use to change an infusion set. Generally speaking, non-delivery alarms can be categorized as reminders for a user to perform tasks that do no directly affect the immediate delivery of fluid from the infusion pump. Furthermore, the specific example of delivery alarms and non-delivery alarms is intended to be exemplary and should not be construed as limiting.

FIG. 3A is an exemplary depiction of controller 102, in accordance with an embodiment of the present invention. The controller 102 is contained within a case 300 and is generally proportioned to be held in a single hand. The controller 102 includes a screen 306 that in some embodiments is touch sensitive and can be used as the primary interface for a user interface displayed on the screen 306. The orientation of the screen 306 in a portrait mode, as shown in FIG. 3A, should not be perceived as limiting as other embodiments of the controller 102 can have the screen 306 oriented in a landscape mode. Alternatively, the controller 102 can include accelerometers that allow images displayed on the screen 306 to transition between portrait and landscape depending on how a user holds the controller 102. Buttons 302a, 302b, and 302c can further be included in some embodiments of the controller 102.

The buttons 302a, 302b and 302c can be used to provide quick access to different elements of the user interface displayed on the screen 306. Exemplary functions that can be assigned to the buttons 302a, 302b and 302c are navigating the user interface to a previous screen, navigating the user interface to a home page, or bringing up a help screen that defines elements currently displayed on the screen 306. While buttons 302a, 302b and 302c are shown, other embodiments of the controller 102 can have fewer buttons, more buttons or even no buttons. In still other embodiments, simultaneously pressing a combination of buttons 302a, 302b and 302c can be associated with particular actions such as automatically muting alarms, powering the controller 102 on or off, rebooting the controller 102, or having the controller 102 enter a diagnostic mode. The particular examples provided are not intended to be limiting and should not be construed to be associated with the simultaneous pressing of buttons. In other embodiments specific sequences of button presses can be used to initiate any of the particular actions discussed above. Furthermore, the location of buttons 302a, 302b and 302c should not be construed as limiting as the case 300 can accommodate the buttons in a variety of locations.

Figure 3B:
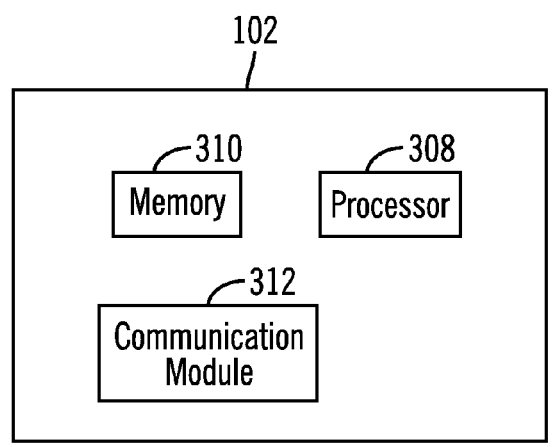
FIG. 3B is an exemplary block diagram showing select elements within the controller, in accordance with one embodiment of the present invention.

FIG. 3B is an exemplary block diagram showing select elements within the controller 102, in accordance with one embodiment of the present invention. The elements discussed below are intended to be exemplary and are not representative of every element within the controller 102. The controller 102 includes a processor 308 that is coupled to a memory 310. In some embodiments the memory 310 is representative of both static RAM and dynamic RAM. Thus, the memory 310 is used to store program instructions that are executed by the processor 308. The program instructions that can be stored in the memory 310 include instructions that render and control a graphical user interface and instructions that allow the controller to communicate with an associated infusion pump (not shown). The memory 310 may also be used to store information specific to a user such as a CIR or an ISF. The dynamic RAM portion of memory 310 can be used to temporarily hold data such as display data that is to be displayed on the screen.

The controller 102 further includes a communication module 312. The communications module 312 includes at least one radio that enables wireless communication with the infusion pump. In other embodiments the communication module 312 includes a plurality of radios that are able to transmit and receive in various communication protocols such as, but not limited to, BlueTooth, WiFi, CDMA, WiMAX, GSM, LTE and the like. In additional embodiments, the communications module 312 is further configured to receive data from a continuous glucose monitoring system. In such embodiments, this allows the controller 102 to receive data from a continuous glucose monitoring system and recommend therapy that can be implemented by the infusion pump.

The graphic user interface displayed on the screen 306 in conjunction with the communication module 312 allows a user to interface and program the infusion pump 104 (FIG. 2). In some embodiments the controller 102 includes multiple profiles that permit different users to exercise different levels of programming control of the infusion pump 104. For example, by entering a password or personal identification number (PIN), a physician could access levels of programming control that are inaccessible to a general user. Similarly, in situations where the infusion pump is worn by a child, the controller 102 can include a parental mode that allows a parent access to programming control that is inaccessible to the child.

For example, in the situation where a very young child using the infusion pump is attending school a parent may wish to program the infusion pump to vibrate for all non-delivery alarms. Non-delivery alarms can include, but are not limited to reminders to check blood glucose values, reminders to eat, reminders to calibrate an associated sensor and the like. Because vibration alarms have become more prevalent with the widespread usage of mobile phones, vibration alerts for non-delivery alarms allows the user of the infusion pump to remain somewhat discrete and can minimize distraction in the classroom. In other embodiments non-delivery alarms may be associated with visual signals (blinking and/or flashing lights), tactile (vibration), audible sounds or any combination thereof.

The communications module 312 within the controller 102 can be used in conjunction with the infusion pump radio (206 of FIGS. 2A and 2B) to establish a relative proximity between the controller and the infusion pump. As will be discussed in further detail below, the relative proximity between the controller and infusion pump can be used to automatically modify alarm setting of the infusion pump.

Figure 4A:
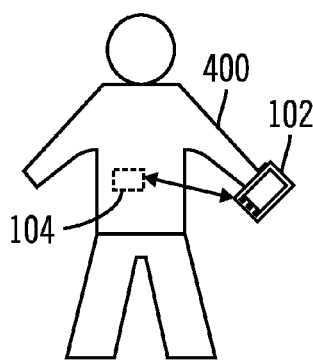
FIGS. 4A and 4B illustrate an exemplary use of the controller with the infusion pump on a user, in accordance with one embodiment of the present invention.
Figure 4B:
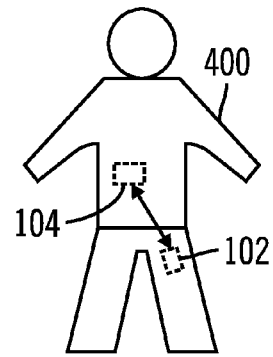

FIGS. 4A and 4B illustrate an exemplary use of the controller 102 with the infusion pump 104 on a user 400, in accordance with one embodiment of the present invention. In FIG. 4A the user 400 is shown wearing an infusion pump 104 under their clothing while holding the controller 102. The distance between the controller 102 and the infusion pump 104 is a distance X. In the embodiment shown, the distance X is within the threshold distance such that the configurable alarm conditions of the infusion pump remain as previously programmed by the user 400.

Figure 5:
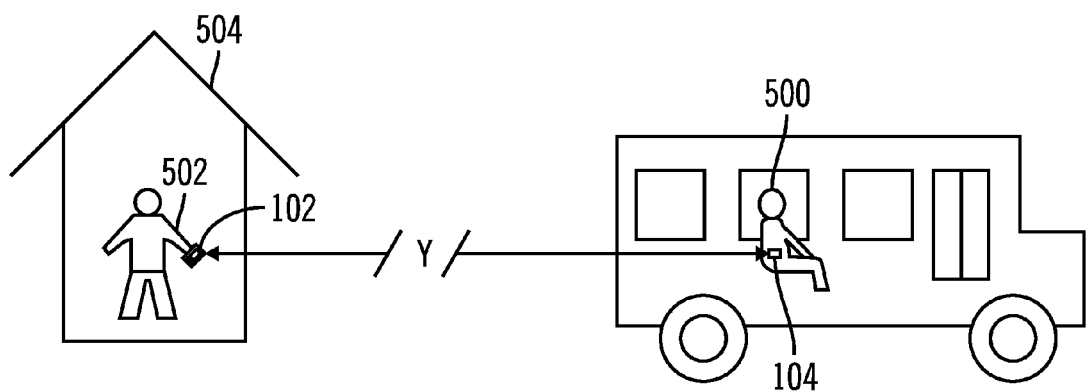
FIG. 5 illustrates a user wearing the infusion pump while the controller remains with a person, in accordance with one embodiment of the present invention.

FIG. 5 illustrates a user 500 wearing the infusion pump 104 while the controller 102 remains with a person 502, in accordance with one embodiment of the present invention. FIG. 5 depicts user 500 wearing infusion pump 104 while the controller 102 remains with person 502 in location 504. As shown, the controller 102 and the infusion pump 104 are separated by a distance Y. In one embodiment of FIG. 5, the distance Y exceeds the threshold distance thereby automatically disabling or changing the programming of the infusion pump 104. In an embodiment where the infusion pump 104 includes controls that can modify the pump setting this feature can be extremely useful in providing peace of mind to parents or caregivers. When the infusion pump 104 is separated from the controller 102 by the threshold distance it is possible to automatically lock out particular changes to the programming of the infusion pump. In case of an emergency, a second controller kept by a school nurse or teacher could be paired with the infusion pump and upon entry of an access code, allow the infusion pump to be reprogrammed. When the distance Y between the infusion pump 104 and the controller 102 returns to a value that is below the threshold value, it is possible to automatically enable programming of the infusion pump 104 using the controls on the infusion pump.

In another embodiment, when the infusion pump 104 is beyond the specified distance Y it is possible to automatically deactivate or mute specific alarms while leaving other alarms active. This feature could be advantageous if the user 500 wishes to maximize discretion in any number of environments where having audible, visual, or vibratory alarms could be a distraction. For example, this would allow a user to automatically mute or deactivate vibration alarms by leaving the controller in their office while attending a meeting in a conference room that is at least the threshold distance from their office. Likewise, a child could attend classes at school while the controller remains with a parent at home, or even with at the teacher's desk (assuming the teacher's desk and the child's desk are separated by the threshold distance). In another scenario, this feature would enable a user to leave the controller in a vehicle while attending a concert or movie knowing that the non-critical vibration, audible, and visual alarms are automatically deactivated when the user is separated from the controller by the threshold distance.

In still another embodiment where the controller 102 is associated with both the pump 104 and a sensor for a Continuous Glucose Monitor (CGM), when the controller is beyond the specified distance Y to either or both the controller 102 or CGM sensor, the pump can be programmed to automatically suspend delivery of the infusion fluid and enter a CGM only mode. While in CGM only mode, in some embodiments the controller 102 would be configured to display and record glucose values as measured by the associated sensor. In one embodiment, this would result in automatic suspension of all fluid infusion while allowing the controller to receive and display sensor glucose data from the CGM sensor. This feature could be implemented when a user is traveling by airplane to avoid possible complications with the infusion pump due to rapid changes in cabin pressure associated with ascent and descent of the aircraft. In other embodiments, the user can manipulate the user interface of the controller 102 to manually enter an "airplane mode" that suspends delivery of the infusion fluid and places the controller in a CGM only mode.

In some embodiments manually entering airplane mode for the controller 102, pump 104 and CGM sensor allows a user to manually enter an expected departure and/or arrival time. The expected departure and arrival times are then associated with alarms from the controller that remind the user that they may resume or suspend infusing fluid from the pump.

In similar embodiments of the CGM only mode, glucose values would be recorded but not necessarily constantly displayed on the controller 102 in order to extend battery life of the controller 102. In such an embodiment, the controller 102 would be able to receive data from the associated glucose sensor but the display for the controller 102 would not necessarily show the data. In order to have the controller display the most recent data and historical data recorded by the associated sensor, a user could press a button on the controller 102. In another embodiment other user operations such a entering a Personal Identification Number (PIN) via a touch-screen would enable display of sensor data. In still other embodiments a user could swipe their finger across the screen in a predefined or user defined pattern to enable display of the sensor data.

Figure 6:
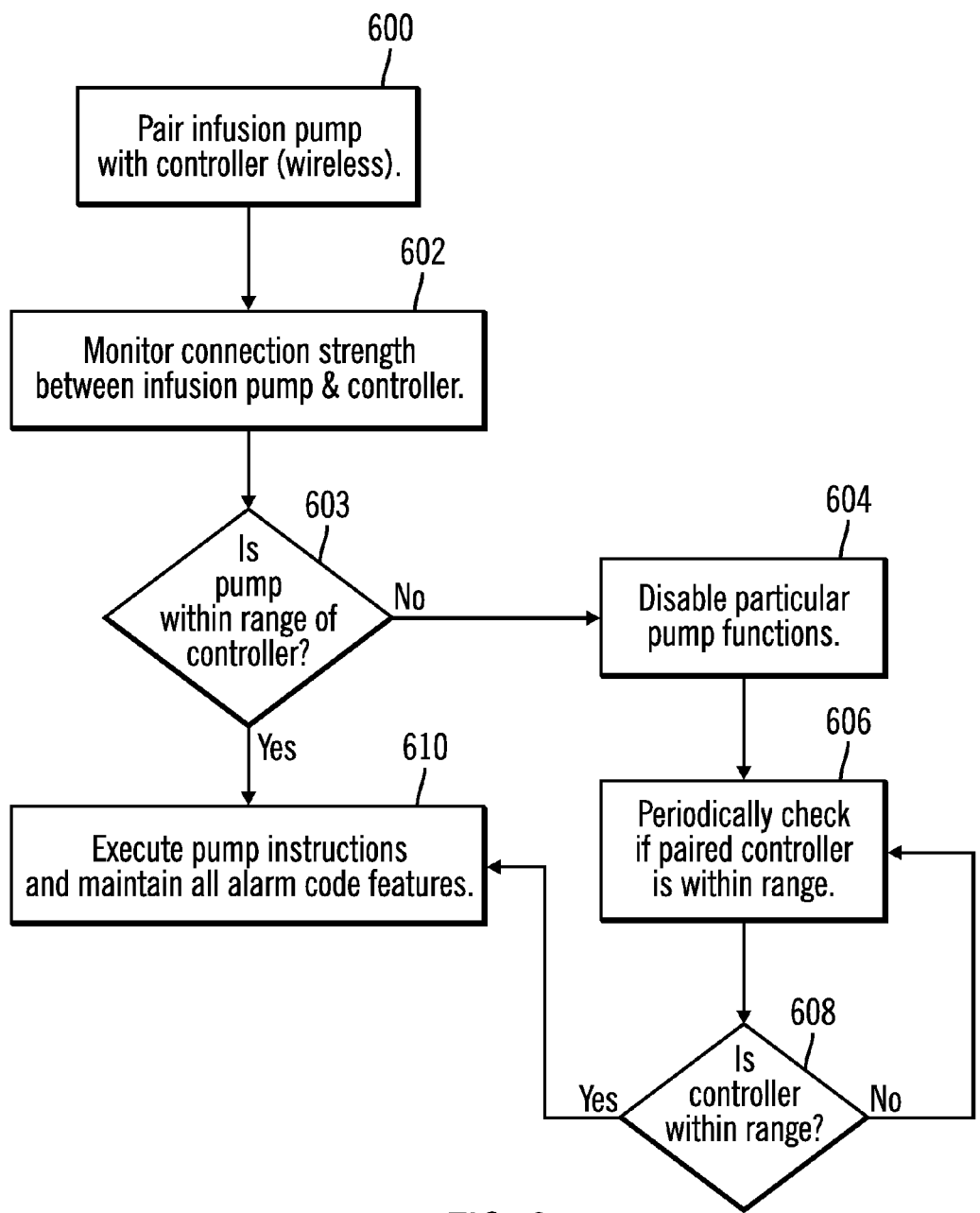
FIG. 6 is a flow chart illustrating a procedure that automatically disables non-delivery alarms when a relative distance between a controller and an infusion pump is exceeded, in accordance with one embodiment of the present invention.

FIG. 6 is a flow chart illustrating a procedure that automatically disables non-delivery alarms when a relative distance between a controller and an infusion pump is exceeded, in accordance with one embodiment of the present invention. The procedure is initiated with operation 600 that pairs an infusion pump with a controller. The pairing of the infusion pump and the controller can be accomplished using well known wireless pairing standards such as, but not limited to BLUETOOTH. Alternatively, a proprietary communication standard that is capable of secured wireless data transfer can be used. Though not shown in FIG. 6, the infusion pump and/or controller may need to be configured to in order to define specific non-delivery alarms that will be automatically disabled. Additionally, in some embodiments, a user will be able to configure the relative distance threshold between the controller and infusion pump that must be exceeded before automatically disabling the non-delivery alarms. In some embodiments the controller is used to program or define the non-delivery alarms and the relative distance. In other embodiments either the controller or the infusion pump can be used to define the relative distance threshold and the non-delivery alarms that are disabled with the threshold distance is exceeded.

Operation 602 monitors the relative distance between the controller and the infusion pump. As previously discussed, in one embodiment the relative distance can be determined based on relative signal strength of bi-directional communications between the infusion pump and the controller. Regardless of how the relative distance is determined, operation 603 determines if the infusion pump and paired controller are within the specified relative distance. If operation 603 determines that that infusion pump is beyond the specified relative distance, operation 604 automatically disables the previously specified infusion pump alarms. In other embodiments, operation 604 can also be used to automatically disable specified functionality of the infusion pump.

Operation 606 periodically checks if the paired controller is within the threshold distance. In one embodiment the controller periodically broadcasts a query that can be answered by the paired infusion pump. In other embodiments the infusion pump periodically broadcasts a query that can be answered by the paired controller. As previously discussed, whether the infusion pump or the controller answers or responds to a broadcast query can be based on the relative signal strength of the broadcast signal which can be used to determine if the controller is within a specified distance. In this embodiment operation 608 determines if the controller is within the threshold distance. If the controller is within the threshold distance, operation 610 executes pump instructions and maintains all of the alarm code features. In order to determine if the controller has moved beyond the threshold distance since the previous check, the procedure can periodically return to operation 602.

For example, with embodiments where controls for the infusion pump are found on both the infusion pump and the controller, it would be possible to disable access to specific pump settings in order to minimize the likelihood of accidentally modifying delivery therapy. Such an embodiment could lock out critical elements of the infusion pump programming thereby minimizing the likelihood of a young child accidently modifying the therapy provided by the infusion pump. For example, when the relative distance between an infusion pump programmed to deliver a basal rate of insulin and the paired controller exceeds the threshold value, the insulin pump automatically disables the ability to modify the basal rate via the user interface of the infusion pump.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An infusion system to administer a fluid, the infusion system comprising:
an infusion pump having a pump processor, a pump memory and a pump radio to enable bi-directional communication, the pump memory storing a plurality of configurable alarm conditions;
and a controller having a controller processor, a controller memory, a controller radio to transmit and receive communication from the pump radio, the controller further having a graphical user interface shown on a display, and controls to manipulate the graphical user interface, the bi-directional communication between the infusion pump and the controller establishing an infusion pump relative proximity between the infusion pump and the controller such that when the infusion pump relative proximity exceeds a pump threshold distance at least one of the plurality of configurable alarm conditions of the infusion pump is deactivated.

2. An infusion system as described in claim 1, wherein the modification of the at least one of the plurality of configurable alarm conditions is automatic when the relative proximity exceeds the threshold distance.

3. An infusion system as described in claim 1, wherein user interaction with the controller is required to confirm modification of the at least one of the plurality of configurable alarm conditions.

4. An infusion system as described in claim 1, wherein user interaction with the infusion pump is required to confirm modification of the at least one of the plurality of configurable alarm conditions.

5. An infusion system as described in claim 2, wherein the at least one plurality of configurable alarm conditions is a non-delivery alarm.

6. An infusion system as described in claim 1, wherein when the relative proximity no longer exceeds the threshold distance the at least one of the plurality of configurable alarm conditions of the infusion pump is reactivated.

7. An infusion system as described in claim 6, wherein the reactivation of the at least one of the plurality of configurable alarm conditions of the infusion pump is automatic.

8. An infusion system as described in claim 1, further comprising: a sensor assembly having a sensor placed within an analyte, the sensor assembly further having a sensor radio to enable bi-directional communication with the controller and provide continuous monitoring of the analyte,
the analyte being within subcutaneous tissue of a user, the sensor radio remaining outside of the user.

9. An infusion system as described in claim 8, wherein the bi-directional communication between the sensor assembly and the controller establish a sensor relative proximity defined by a distance between the controller and the sensor assembly.

10. An infusion system as described in claim 9, wherein value fluid delivery from the infusion pump is suspended while continuous monitoring of the analyte continues, when the infusion pump relative proximity exceeds the pump threshold distance.

11. An infusion system as described in claim 10, wherein data from the continuing continuous monitoring is stored in the controller memory.

12. An infusion system as described in claim 11, wherein the controller processor executes stored program instructions to enable the continuous monitoring data stored in the controller memory to be shown on the display.

13. An infusion system to administer a fluid, the infusion system comprising:
an infusion pump having a pump processor, a pump memory and a pump radio to enable bi-directional communication, the pump memory storing a plurality of configurable alarm conditions;
a sensor assembly having a sensor to be placed within an analyte, the sensor assembly further having a sensor radio to enable bi-directional communication with the controller and provide continuous monitoring of the analyte; and
a controller having a controller processor, a controller memory, a controller radio to transmit and receive communication from the pump radio, the controller further having a graphical user interface shown on a display, and controls to manipulate the graphical user interface, the bi-directional communication between the infusion pump and the controller establishing an infusion pump relative proximity between the infusion pump and the controller such that when the infusion pump relative proximity exceeds a pump threshold distance a prompt is delivered to request user confirmation to deactivate at least one of the plurality of configurable alarm conditions of the infusion pump.

14. An infusion system as described in claim 13, wherein the pump threshold distance is defined using the user interface of the controller.

15. An infusion system as described in claim 13, wherein deactivation of the at least one of the plurality of configurable alarm conditions is completed upon user confirmation.

16. An infusion system as described in claim 15, wherein continuous monitoring of the analyte continues after the at least one of the plurality of configurable alarm conditions is deactivated.

* * * * *